US00PP10539P

United States Patent [19]

Fantom

[11] Patent Number: Plant 10,539

[45] Date of Patent: Aug. 4, 1998

[54] KALANCHOE PLANT NAMED 'PINK CARNATION'

[76] Inventor: John William Fantom, 11104 Old Carriage Rd., Glen Arm, Md. 21057-9416

[21] Appl. No.: 818,834

[22] Filed: Mar. 14, 1997

[51] Int. Cl.[6] ..... A01H 5/00

[52] U.S. Cl. ..... Plt./87.15

[58] Field of Search ..... Plt./87.15

[56] References Cited

U.S. PATENT DOCUMENTS

P.P. 5,254 7/1984 Mikkelsen ..... Plt./87.15

*Primary Examiner*—James R. Feyrer

*Assistant Examiner*—Kent L. Bell

*Attorney, Agent, or Firm*—C. A. Whealy

[57] ABSTRACT

A distinct cultivar of Kalanchoe plant named 'Pink Carnation', characterized by its dark hot pink fringed flowers with white margins giving a bi-colored appearance; moderately vigorous plant growth habit and moderate growth rate; upright plant habit; dark green and glossy leaves; floriferous with numerous flowers per plant; and good postproduction longevity.

2 Drawing Sheets

The present invention relates to a new and distinct cultivar of Kalanchoe plant, botanically known as *Kalanchoe blossfeldiana* Adans., and hereinafter reffered to by the cultivar name Pink Carnation.

The new cultivar was discovered by the inventor in 1992 as a naturally-occurring mutation of the Kalanchoe cultivar 'Royalty' (disclosed in U.S. Plant Pat. No. 5,254) in a greenhouse in Baltimore, Md.

Asexual reproduction of the new cultivar by terminal cuttings taken at Baltimore, Md., has shown that the unique features of this new Kalanchoe are stable and reproduced true to type in successive generations.

The cultivar 'Pink Carnation' has not been observed under all possible environmental conditions. The phenotype may vary somewhat with variations in environment such as temperature, daylength and light intensity, without, however, any variance in genotype. The following observations, measurements and comparisons describe plants grown during the winter in West Chicago, Ill., under commerical practice in a glass-covered greenhouse.

The following traits have been repeatedly observed and are determined to be the unique characteristics of 'Pink Carnation'. These characteristics in combination distinguish 'Pink Carnation' as a new and distinct cultivar:

1. Dark hot pink fringed flowers with white margins giving a bi- colored appearance.
2. Moderately vigorous plant growth habit and moderate growth rate.
3. Upright plant habit.
4. Dark green and glossy leaves.
5. Suitable for various container sizes from 10 to 15 cm.
6. Floriferous with numerous flowers per plant.
7. Good postproduction longevity.

Plants of the new Kalanchoe are similar to plants of the cultivar 'Royalty' in foliage and leaf characteristics. Plants of the new Kalanchoe differ from plants of the culivar 'Royalty' in the following characteristics:

1. Flowers of plants of the new Kalanchoe have lacerate or fringed petals that overlap whereas flowers of plants of the cultivar 'Royalty' have petals with entire margins and petals that do not overlap.
2. Flowers of plants of the new Kalanchoe are dark hot pink with a white margin which gives a bi-colored appearance whereas flowers of plants of the cultivar 'Royalty' are solid dark hot pink in color.

3. Flowers of plants of the new Kalanchoe are larger than flowers of plants of the cultivar 'Royalty'.
4. Flowers of plants of the new Kalanchoe are longer-lasting than flowers of plants of the cultivar 'Royalty'.

The accompanying colored photographs illustrate the overall appearance of the new cultivar, showing the colors as true as it is reasonably possible to obtain in colored reproductions of this type.

The first photograph comprises a top perspective view of a typical potted plant of 'Pink Carnation'.

The second photogroaph is a close-up view of typical flowers of 'Pink Carnation'. Flower and foilage colors in the photograph may appear different from the actual colors due to light reflectance.

In the following description, color references are made to The Royal Horticultural Society Colour Chart except where general terms of ordinary dictionary signifiacance are used. Measurements and numerical values represent averages for six typical plants in 10.5 cm containers that were grown during the months of October to January. Plants were exposed to four weeks of long day/short nights followed by nine weeks of short day/long night photoperiodic treatments.

Botanical Classification: *Kalanchoe blossfeldiana* Adans. cultivar 'Pink Carnation'.

Parentage: Naturally-occurring mutation of *Kalanchoe blossfeldiana* Adans. cultivar 'Royalty' (disclosed in U.S. Plant Pat. No. 5,254).

Propagation:

*Type cutting.*—Terminal cuttings.

*Time to initiate roots.*—Summer: About 12 days at 24° C. Winter: About 18 days at 18° C.

*Rooting habit.*—Numerous, fine, fibrous, and well branched.

Plant description:

*Shape.*—Upright, inverted triangle.

*Branching habit.*—Moderate branching, generally shoots formed at every node.

*Plant size at flowering.*—About 25 cm from soil level to top plant, about 32 cm in diameter, appropriate for 10 to 15 -cm containers.

*Vigor.*—Moderately vigorous and moderate growth rate.

*Crop time.*—Three to 4 weeks of long day/short night conditions followed by 9 to 12 weeks of short day/long night conditions are required to produce flowering plants. Depending on temperature and light levels, a total of 12 to 16 weeks is required.

*Foliage description.*—Leaves simple, opposite, generally symmetrical. Size: Length: About 13 cm. Width: About 10 cm. Shape: Ovate. Apex: Obtuse. Base: Acute. Margin: Crenate. Texture: Leathery, glabrous, glossy coriaceous and succulent. Petiole length: About 3.5 cm. Color: Young foliage adaxial surface: 147A. Young foliage abaxial surface: 146A. Mature foliage adaxial surface: Darker than 147A. Petiole: Greener than 146A. Stem color: 146A.

Flower Description:

*Flower type and habit.*—Single flowers arranged in panicles, compound dichasial cymes on strong peduncles. Freely flowering, very floriferous with new buds continuing to develop.

*Natural flowering season.*—Autumn/winter in Northern Hemisphere. Flower initiation and development can be induced under short day/long night conditions. Opening of new buds will continue for at least six weeks. Individual flowers last about 16 days after opening. Flowers persistent.

*Inflorescences borne.*—Above foliage, arising from leaf axils. Inflorescence of each shoot is formed by dichotomous branching.

*Time to flower.*—Under warm growing temperatures, 25° C., plants of the new Kalanchoe will start flowering after about 9 weeks of exposure to controlled photoperiods (short day/long night conditions). Under cooler growing temperatures, 20° C., plants of the new Kalanchoe will flower after about 12 weeks of exposure to controlled photoperiods. First flower open is the terminal flower at the main axis and is followed by the opening of the terminal flowers of the side branches of the inflorescence.

*Flower diameter.*—About 1.7 cm.

*Flower depth height.*—About 1.5 cm.

*Quantity.*—More than 150 flowers per plant.

*Flower buds.*—Size: Length: About 1.5 cm. Width: About 5 mm. Shape: Oblong becoming tubular/ovoid with development. Rate of opening: Rapid. Color: Intitally green, 144A, becoming pinkish green just before opening than pink, 57D.

*Petals*—Quantity: Four, fused at base and overlapping. Size: Length: 8 to 10 mm. Width: 8 to 10 mm. Shape: Rounded. Apex/margin: Lacerate, fringed. Texture: Glabrous, smooth and satiny. Aspect: Slightly cupped. Color: When opening, adaxial surface: 57A with white margin. When opening, abaxial surface: 57D. Mature, adaxial surface: 57A with white margin. Mature, abaxial surface:57D to 58D. Throat: Green, 144B, with pink tones. Tube: Green 144A, with pink tones.

*Sepals.*—Quantity: Four. Size: Length: About 8mm. Width at base: About 3 mm. Shape: Linear. Apex: Pointed. Margin: Entire. Texture: Glabrous. Aspect: Upright. Color: Adaxial surface: 144A, red at apex. Abaxial surface: 144A.

*Peduncle.*—Aspect: Strong, erect and rigid. Length: 3 to 5 mm. Texture: Glabrous. Color: 146A.

*Reproductive organs.*—Stamens: Stamen number: Eight. Anther size: 0.3 to 0.5 mm. Anther shape: Flat oblong. Pollen color: yellow, close to 12 B. Amount of pollen: Moderate. Pistils: Pistil number: Four. Stigma shape: Flat. Stigma color: Light yellow, close to 9D. Style length: 9 to 10 mm. Style color: 144A.

Disease resistance: No known Kalanchoe diseases observed to date under commercial production conditions.

Seed production: Seed production has not been observed.

It is claimed:

1. A new and distinct cultivar of Kalanchoe plant named 'Pink Carnation', as illustrated and described.

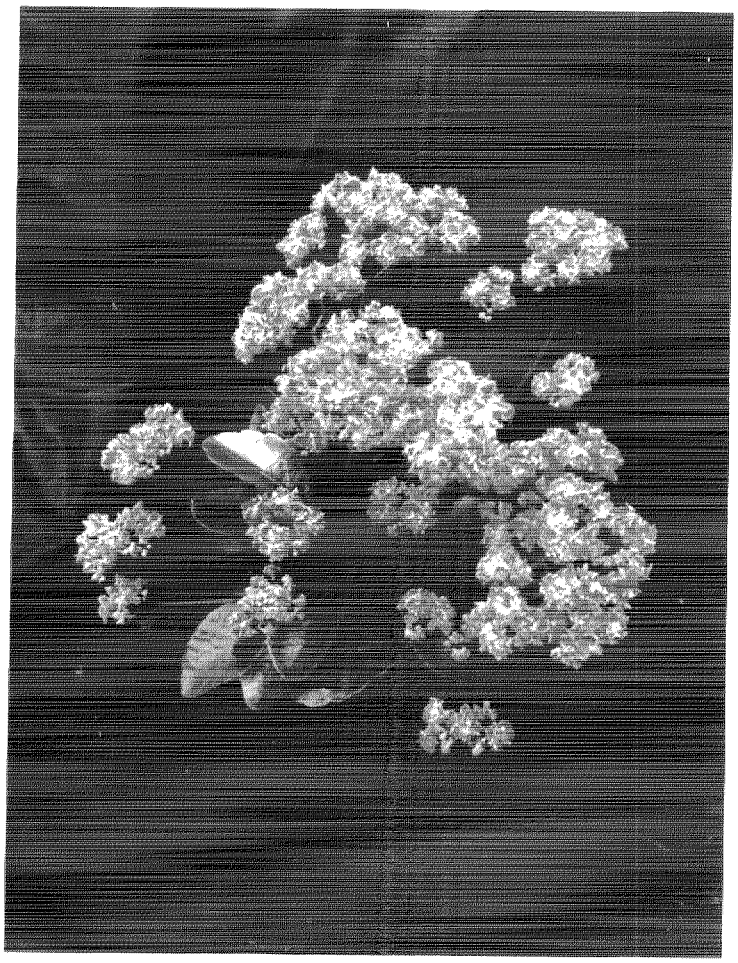

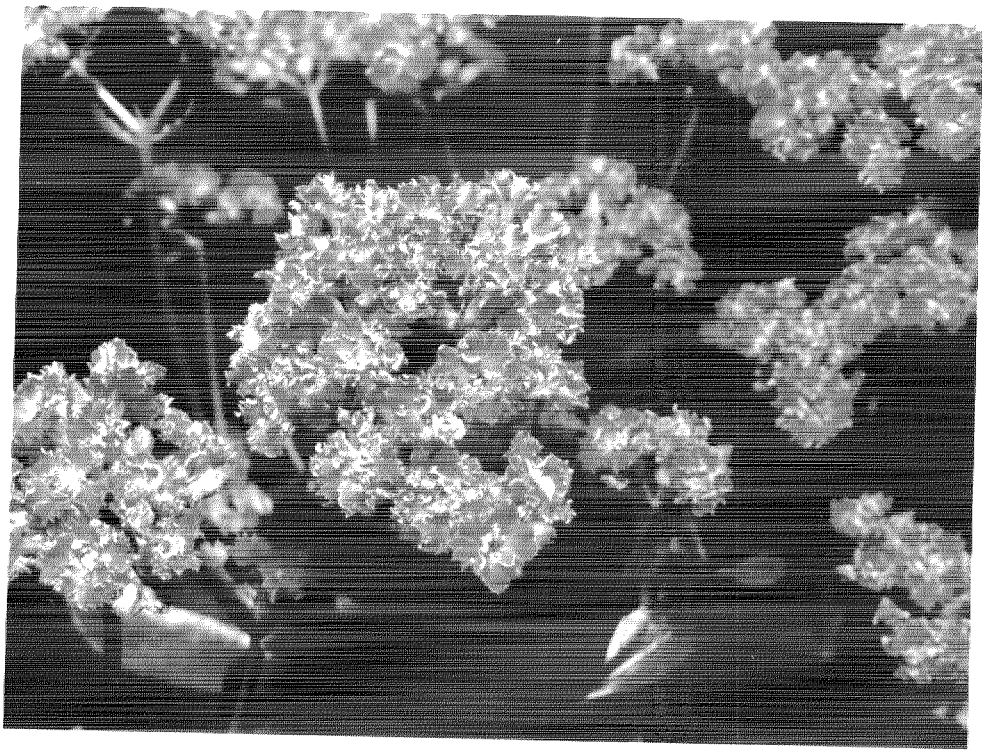

* * * * *